(12) United States Patent
Gray et al.

(10) Patent No.: US 8,375,956 B2
(45) Date of Patent: Feb. 19, 2013

(54) EYE REGISTRATION SYSTEM FOR REFRACTIVE SURGERY AND ASSOCIATED METHODS

(75) Inventors: Gary P. Gray, Orlando, FL (US); John A. Campin, Orlando, FL (US)

(73) Assignee: Alcon Refractivehorizons, Inc., Fort Worth, TX (US)

( * ) Notice: Subject to any disclaimer, the term of this patent is extended or adjusted under 35 U.S.C. 154(b) by 82 days.

(21) Appl. No.: 12/777,325

(22) Filed: May 11, 2010

(65) Prior Publication Data

US 2010/0220181 A1  Sep. 2, 2010

Related U.S. Application Data

(62) Division of application No. 10/999,268, filed on Nov. 30, 2004, now Pat. No. 7,815,631.

(51) Int. Cl.
  *A61B 19/00* (2006.01)
  *A61B 18/18* (2006.01)
(52) U.S. Cl. .......... 128/898; 606/4; 606/5; 351/212
(58) Field of Classification Search .......... 606/4, 5, 606/10–12; 351/205–212; 128/898
  See application file for complete search history.

(56) References Cited

U.S. PATENT DOCUMENTS

| | | | |
|---|---|---|---|
| 4,476,862 A | 10/1984 | Pao | |
| 4,705,035 A | 11/1987 | Givens | |
| 4,739,761 A | 4/1988 | Grandon | |
| 5,029,220 A | 7/1991 | Juday | |
| 5,098,426 A | 3/1992 | Sklar et al. | |
| 5,196,873 A | 3/1993 | Yamanobe et al. | |
| 5,345,281 A | 9/1994 | Taboada et al. | |
| 5,485,404 A | 1/1996 | Shindo | |
| 5,531,753 A | 7/1996 | Oliveira | |
| 5,568,208 A | 10/1996 | Van de Velde | |
| 5,620,436 A | 4/1997 | Lang et al. | |
| 5,638,176 A | 6/1997 | Hobbs et al. | |
| 5,645,550 A | 7/1997 | Hohla | |
| 5,865,832 A * | 2/1999 | Knopp et al. | .......... 606/10 |
| 5,892,569 A | 4/1999 | Van de Velde | |

(Continued)

FOREIGN PATENT DOCUMENTS

| | | |
|---|---|---|
| EP | 1845918 | 10/2007 |
| JP | 2003-79657 | 3/2003 |

(Continued)

OTHER PUBLICATIONS

International Search Report for PCT/US2005/042952, Publication No. WO2006/060,323, 4 pages.

(Continued)

*Primary Examiner* — Ahmed Farah
(74) *Attorney, Agent, or Firm* — Keiko Ichiye

(57) ABSTRACT

An orientation method for corrective eye surgery that registers pairs of eye images taken at different times and with the patient in different positions includes retrieving reference digital image data on an eye of the patient, including image data on an extracorneal eye feature. Real-time image data are collected that include image data on the extracorneal eye feature. A combined image is displayed of a superposition of the data sets, and a determination is made as to whether the combined image indicates an adequate registration between them based upon the extracorneal eye feature data in the two data sets. If the registration is not adequate, one of the data sets is manipulated until an adequate registration is achieved. A system is directed to apparatus and software for orienting a corrective program for eye surgery.

22 Claims, 7 Drawing Sheets

U.S. PATENT DOCUMENTS

| | | | |
|---|---|---|---|
| 5,923,399 A | 7/1999 | Van de Velde | |
| 5,943,117 A | 8/1999 | Van de Velde | |
| 5,966,197 A | 10/1999 | Yee | |
| 6,000,799 A | 12/1999 | Van de Velde | |
| 6,027,216 A | 2/2000 | Guyton et al. | |
| 6,129,722 A | 10/2000 | Ruiz | |
| 6,702,806 B2 | 3/2004 | Gray et al. | |
| 6,913,603 B2 | 7/2005 | Knopp et al. | |
| 7,146,983 B1 | 12/2006 | Hohla et al. | |
| 2002/0082590 A1* | 6/2002 | Potgieter | 606/4 |
| 2004/0143244 A1 | 7/2004 | Gray et al. | |
| 2004/0143245 A1 | 7/2004 | Gray et al. | |

FOREIGN PATENT DOCUMENTS

| | | |
|---|---|---|
| WO | WO 01/28476 | 4/2001 |
| WO | WO 01/78584 | 10/2001 |
| WO | WO 02/087442 | 11/2002 |
| WO | WO 03/053228 | 7/2003 |

OTHER PUBLICATIONS

PCT International Preliminary Report on Patentability and Written Opinion, PCT/US2005/042952, Jun. 5, 2007, 8 pages.

* cited by examiner

EYE REGISTRATION SYSTEM FOR REFRACTIVE SURGERY AND ASSOCIATED METHODS

This application is a divisional of and claims priority to U.S. application Ser. No. 10/999,268 filed on Nov. 30, 2004 now U.S. Pat. No. 7,815,631.

TECHNICAL FIELD OF THE INVENTION

The present invention relates to systems and methods for improving objective measurements preceding corrective eye surgery, and, more particularly, to such systems and methods for improving results of corrective laser surgery on the eye.

BACKGROUND OF THE INVENTION

Laser-in-situ-keratomileusis (LASIK) is a common type of laser vision correction method. It has proven to be an extremely effective outpatient procedure for a wide range of vision correction prescriptions. The use of an excimer laser allows for a high degree of precision and predictability in shaping the cornea of the eye. Prior to the LASIK procedure, measurements of the eye are made to determine the amount of corneal material to be removed from various locations on the corneal surface so that the excimer laser can be calibrated and guided for providing the corrective prescription previously determined by the measurements. Refractive laser surgery for the correction of astigmatism typically requires that a cylindrical or quasicylindrical ablation profile be applied to the eye. The long axis of this profile must be properly oriented on the eye in order to accurately correct the visual aberration.

An objective measurement of a patient's eye is typically made with the patient sitting in an upright position while focusing on a target image. A wavefront analyzer then objectively determines an appropriate wavefront correction for reshaping the cornea for the orientation of the eye being examined. The LASIK or PRK procedure is then performed with the patient in a prone position with the eye looking upward.

It is well known that the eye undergoes movement within the socket comprising translation and rotation ("cyclotortion") as the patient is moved It is well known that the eye undergoes movement within the socket comprising translation and rotation ("cyclotortion") as the patient is moved from the upright measuring position to the prone surgery position. Techniques known in the art for accommodating this movement have included marking the eye by cauterizing reference points on the eye using a cautery instrument (U.S. Pat. No. 4,476,862) or caustic substance, a very uncomfortable procedure for the patient. It is also known to mark a cornea using a plurality of blades (U.S. Pat. No. 4,739,761). The application on the scleral surface or the injection of a dye or ink is also used to mark the reference locations to identify the orientation of the eye during measurement, permitting a positioning of the corrective profile to the same orientation prior to surgery. However, the time delay from measurement to surgery often causes the ink to run, affecting the accuracy of an alignment. Making an impression on the eye (U.S. Pat. No. 4,705,035) avoids the caustic effects of cauterizing and the running effect of the ink. However, the impression can lose its definition quickly relative to the time period between the measurement and surgery.

For correction of astigmatism, it is known to mark the cornea preparatory to making the surgical incisions (U.S. Pat. No. 5,531,753).

Tracker systems used during the surgical procedure or simply for following eye movement, while the patient is in a defined position, are known to receive eye movement data from a mark on a cornea made using a laser beam prior to surgery (U.S. Pat. No. 4,848,340) or from illuminating and capturing data on a feature in or on the eye, such as a retina or limbus, for example (U.S. Pat. Nos. 5,029,220; 5,098,426; 5,196,873; 5,345,281; 5,485,404; 5,568,208; 5,620,436; 5,638,176; 5,645,550; 5,865,832; 5,892,569; 5,923,399; 5,943,117; 5,966,197; 6,000,799; 6,027,216).

Commonly owned U.S. Pat. No. 6,702,806, 2004/0143245, and 2004/0143244 address the problem of registering a pre-surgery image with a live eye image with the use of image mapping and manipulation, and also with software for calculating and imposing a graphical reticle onto a live eye image.

BRIEF SUMMARY OF THE INVENTION

The present invention is directed to an orientation system and method for corrective eye surgery that aligns (registers) pairs of eye images taken at different times. An exemplary embodiment of the method comprises the step of retrieving a reference data set comprising stored digital image data on an eye of a patient. The stored image data will have been collected with the patient in a pre-surgical position. These data include image data on an extracorneal eye feature.

A real-time data set is collected that comprises digital image data on the patient eye in a surgical position different from the pre-surgical position. These real-time image data include image data on the extracorneal eye feature.

A combined image is then displayed that comprises a superposition of the reference and the real-time data sets, and a determination is made as to whether the combined image indicates an adequate registration between the reference and the real-time data sets. Such a determination is made based upon the extracorneal eye feature data in the reference and the real-time data sets. If the registration is not adequate, one of the reference and the real-time data sets is manipulated, i.e., translated and/or rotated, until an adequate registration is achieved.

A system of the present invention is directed to apparatus and software for orienting a corrective program for eye surgery. The system includes means for performing the method steps as outlined above, including computer software for achieving the superposition of the reference and the real-time data sets.

Thus an aspect of the present invention provides a system and method for achieving a precise registration of the eye by making sure that an eye feature is positioned in substantially the same location on the superimposed images. As a result, a prescription measurement for reshaping a cornea, for example, will account for the rotation and translation of the eye occurring between measurements made with the patient in a sitting position and laser surgery with the patient in a supine position.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully

DETAILED DESCRIPTION OF THE PREFERRED EMBODIMENTS

A description of the preferred embodiments of the present invention will now be presented with reference to FIGS. 1-6.

Figure 1:
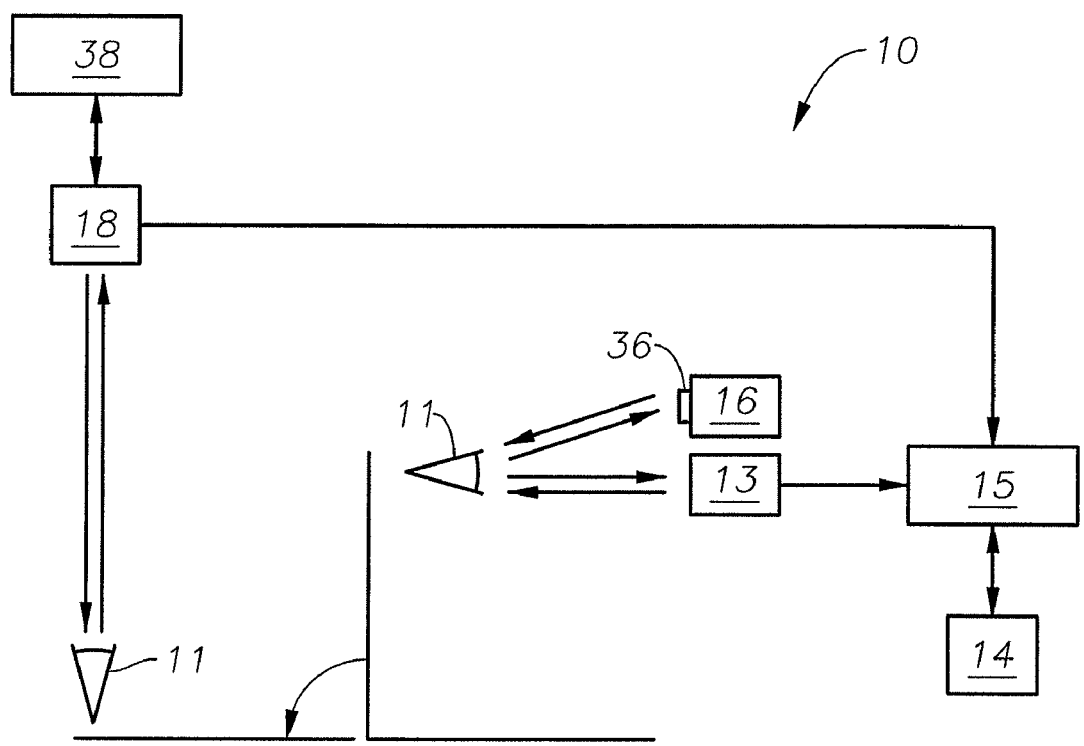
FIG. 1 is a schematic diagram of the system of the first embodiment of the present invention.
Figure 2A:
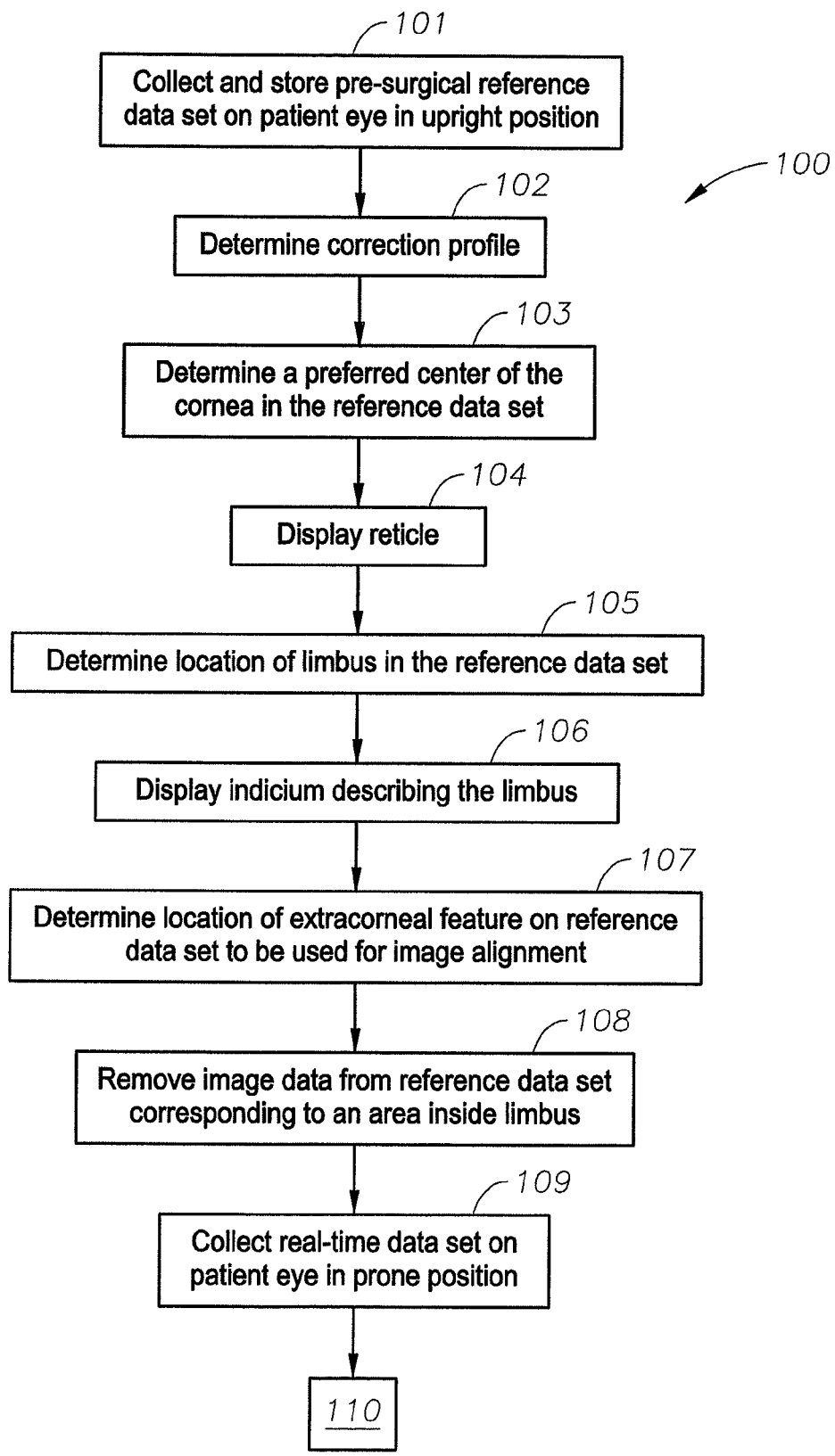
FIGS. 2A, 2B is a block diagram of the data flow.
Figure 2B:
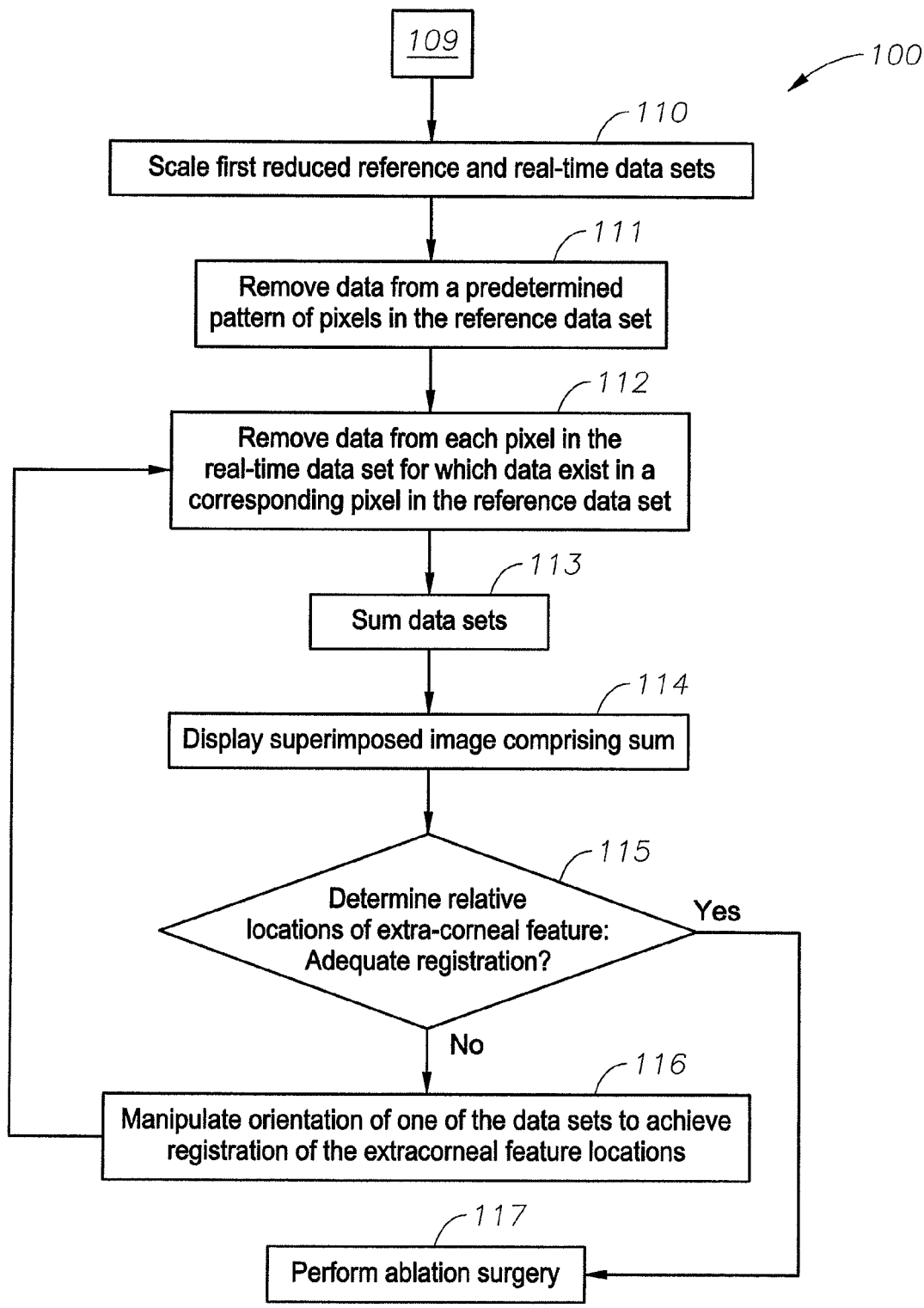
Figure 3:
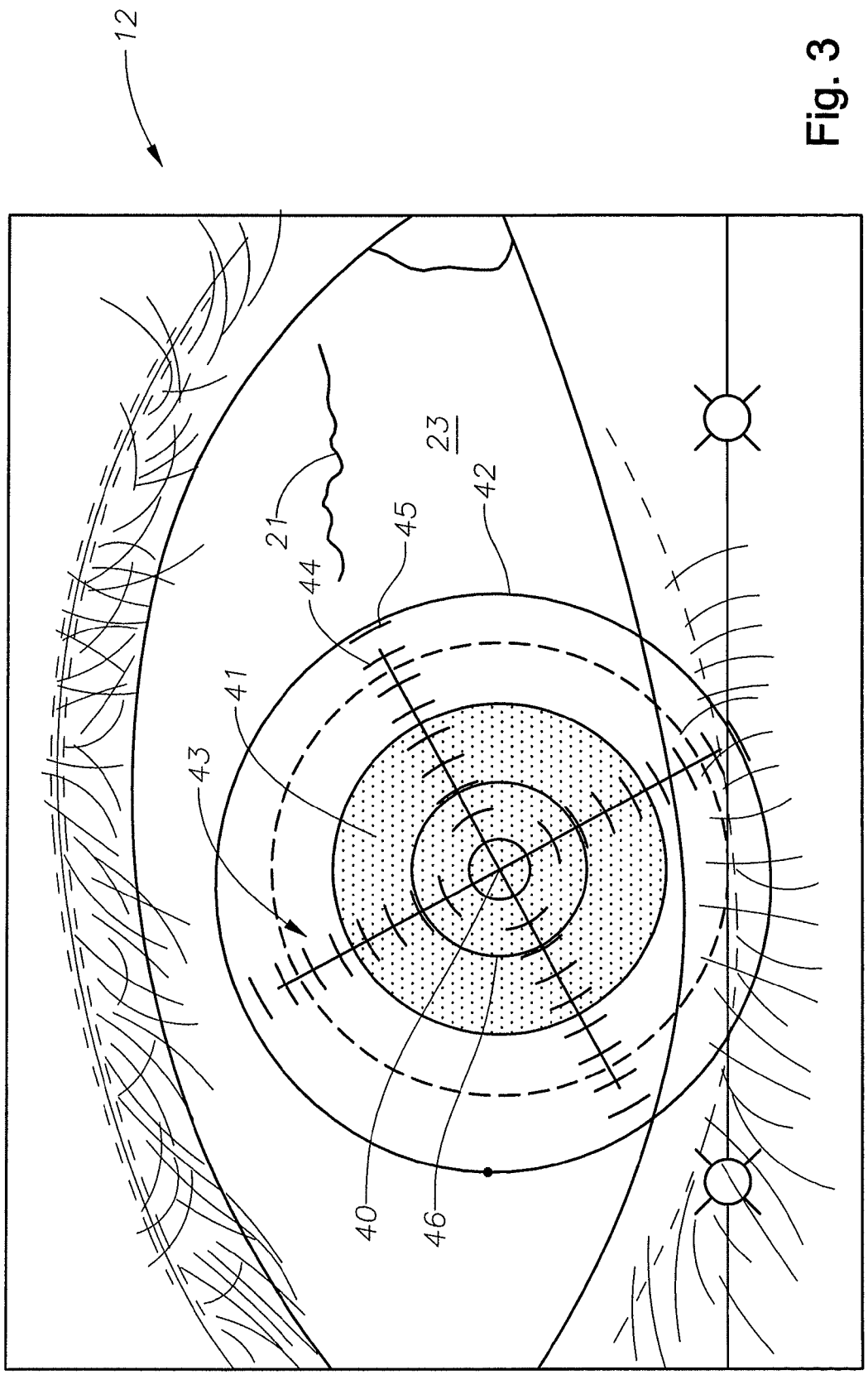
FIG. 3 illustrates the reference data set image.

A schematic diagram of the system 10 of an embodiment of the invention is shown in FIG. 1, data flow of an exemplary embodiment of the method 100 in FIGS. 2A,2B, and displayed images in FIGS. 3-6. In an exemplary embodiment of the system 10, a patient's eye 11 is imaged in a substantially upright position by capturing a first video image 12 using a camera such as a charge-coupled-device (CCD) camera 13 (block 101). Such an image 12 is illustrated in FIG. 3. The first image, comprising a reference data set, is stored in a database 14 in electronic communication with a processor 15.

Next an objective measurement is made on the eye 11 to determine a desired correction profile, using a measurement system 16 such as that disclosed in co-pending application Ser. No. 09/566,668, although this is not intended as a limitation (block 102).

Once the correction profile is determined, the patient is made ready for surgery, and placed in the second position, which is typically prone. Alternatively, the first scan to determine the correction profile may be made in a different location and at a time prior to the surgical procedure, the time interval being, for example, several weeks.

Real-time image data are collected prior to and during surgery using a second camera 18, in communication with a second system 38 for performing surgery, and these data are also stored in the database 14. In a preferred embodiment both the first 13 and the second 18 cameras are adapted to collect color images, and these images are converted using software resident on the processor 15 to pixel data. It is useful to collect color images for viewing by the physician, since preselected identifiable images such as a blood vessel 21 (FIG. 3) are more readily seen within the sclera 23, since the red color of the vessel 21 is clearly identifiable.

Next the surgeon identifies a plurality of features in the eye 11 using a graphical user interface (GUI) while viewing the still image of the eye (FIG. 3). Such features may include a preferred center 40 of the cornea 41 in the reference set (block 103), the location of the limbus 42 (block 105), and the location of an extracorneal feature such as a blood vessel 21 (block 107). The system then generates indicia for display superimposed on the reference data, including a reticle 43 comprising crossed, perpendicular lines 44 with cross-hatching 45 and a central circle 46 centered about the corneal center 40 and smaller than the limbal ring 42, with the crossing point of the lines 44 corresponding to the cornea center 40 (block 104). The indicia also include a ring 47 positioned atop the limbus 42 (block 106).

Figure 4:
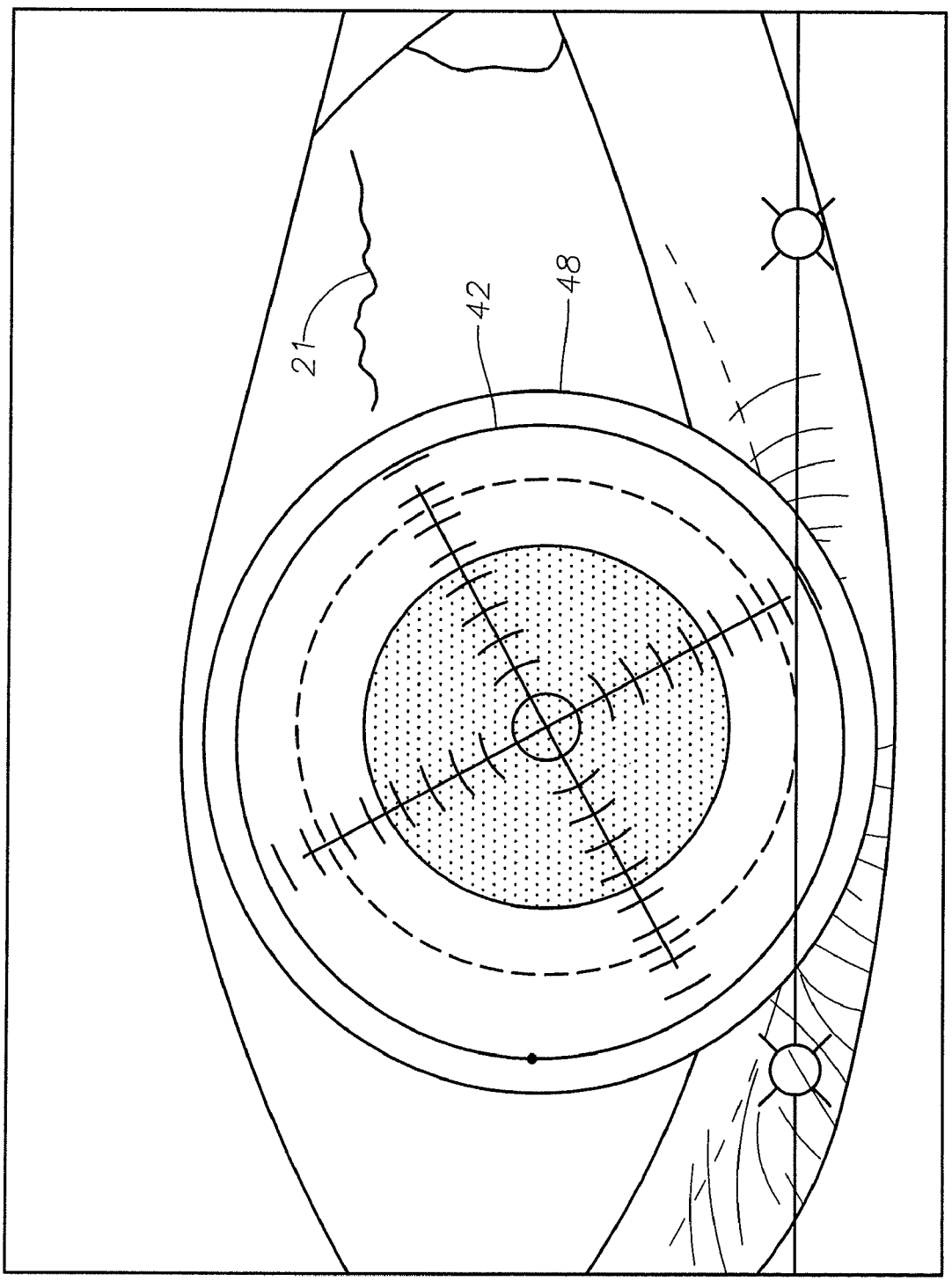
FIG. 4 illustrates the reference data set image of FIG. 3, but with data from a central area including the area inside the limbus removed.

The reference data set is then manipulated by removing pixel data from all pixels circumscribed by the limbus 42 (block 108; FIG. 4), and typically by removing pixel data from an area 48 beyond the limbus 42, to yield a first reduced reference data set.

Prior to and during surgery, a real-time data set comprising real-time digital image data on the patient eye 11 in a surgical position different from the pre-surgical position is collected (block 109). The real-time image data include image data on the blood vessel 21. Next one of the reference and the real-time data sets is scaled to the other of the reference and the real-time data sets (block 110). This scaling is performed in order to equalize a display size of the reference and the real-time data sets for subsequent display in a superimposed image.

Figure 5:
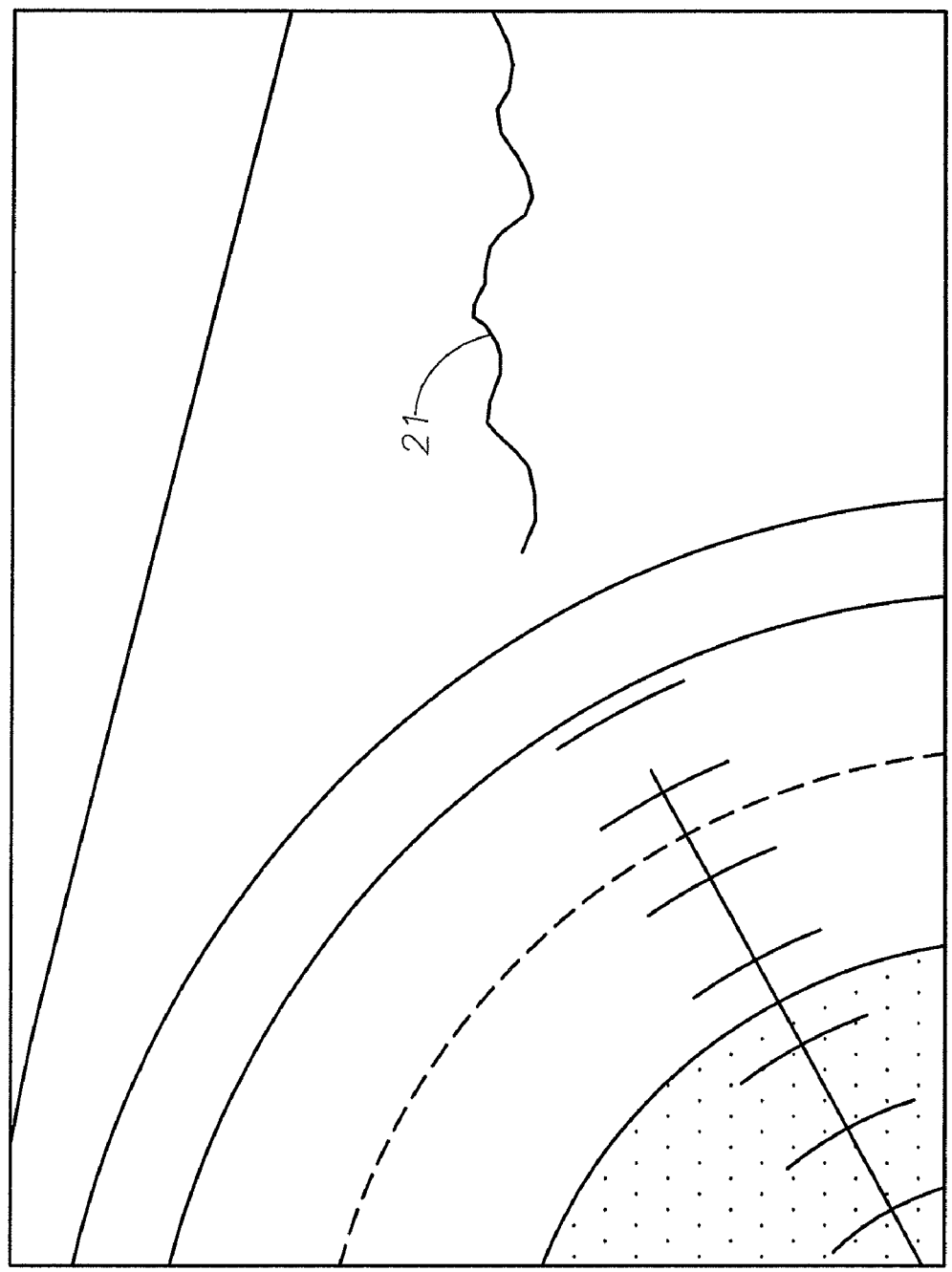
FIG. 5 illustrates a portion of the sampled reference data set image at a higher magnification.

The pixels of the first reduced reference data set are then sampled to result in a second reduced reference data set (block 111; FIG. 5). This sampling preferably takes the form of removing data from a predetermined pattern of pixels, leaving a data set having data in all the pixels except those in the predetermined pattern. An exemplary predetermined pattern comprises alternate pixels. It can be seen that the blood vessel 21 is clearly visible in FIG. 5, thereby indicating that the sampling does not cause a sufficient loss of resolution to interfere with identification of the vessel 21.

The pixels in the real-time data set are then sampled by removing pixel data from a set of pixels in the real-time data set disjoint from those of the second reduced reference data set (block 112) to yield a reduced real-time data set.

Figure 6:
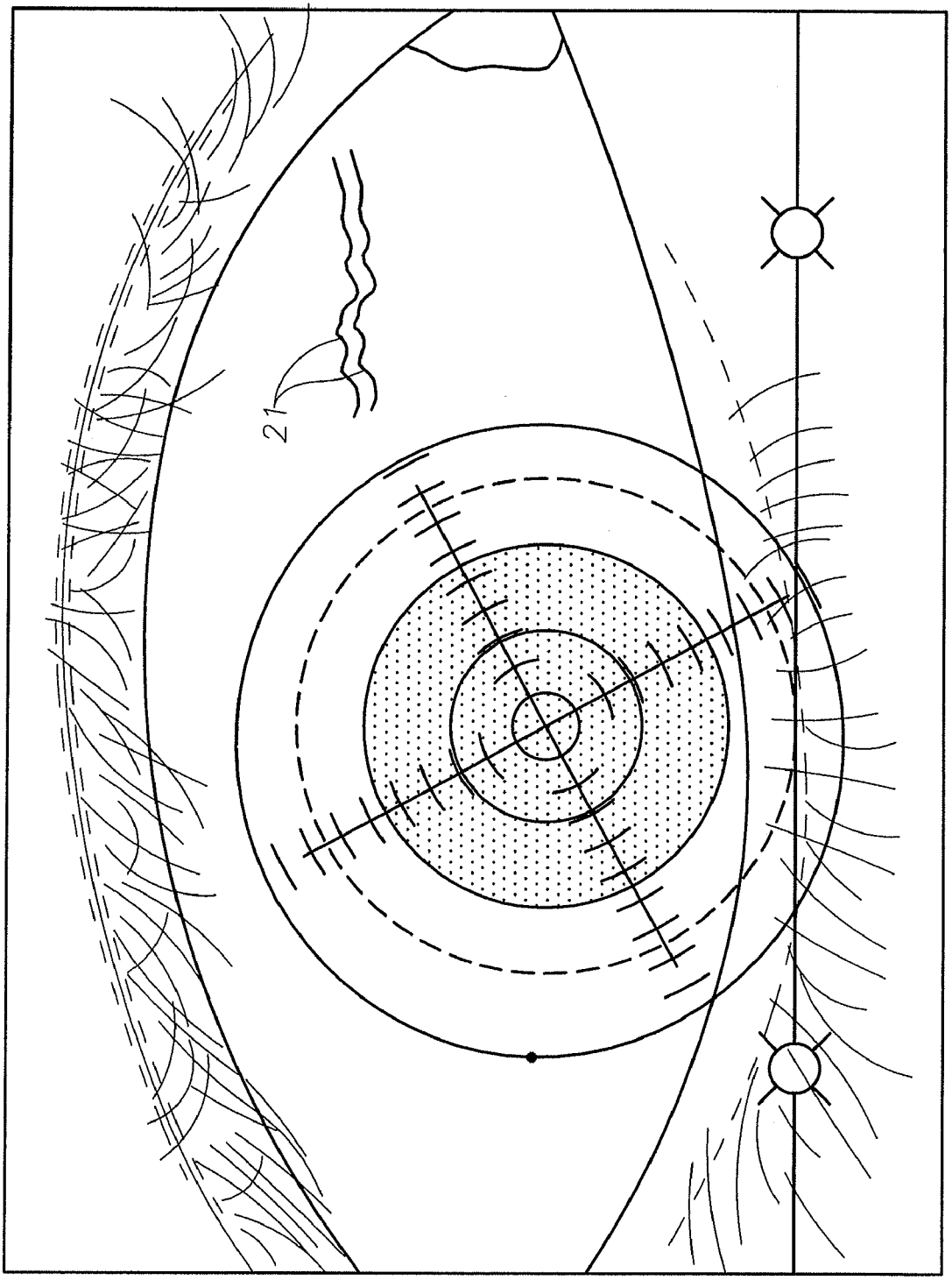
FIG. 6 illustrates the sampled reference data set image of FIG. 5 interdigitated with a sampled real-time data set image.

Next the second reduced reference data set and the reduced real-time data set are summed (block 113), so that each pixel of the summed set contains data from a unitary one of the second reduced reference and reduced real-time data sets. A superimposed image comprising the sum is displayed (block 114; FIG. 6).

Examination of FIG. 6 indicates that the blood vessel 21 images from the second reduced reference and reduced real-time data sets are clearly visible, and that they are not in registry (block 115). In such a case, either an automatic or manual manipulation of one of the data sets is performed (block 116) until adequate registration is achieved (block 115), and the data processing beginning at block 111 is carried out again.

Once registry is considered adequate, the surgical process can begin (block 117), with monitoring continued during surgery. Thus the treatment pattern, typically a laser shot pattern calculated to achieve a desired corneal profile using, for example, an excimer laser, can be modified to account for eye rotation resulting from the patient's movement from upright to prone position.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for orienting a corrective program for eye surgery comprising the steps of:
    retrieving, by one or more processors, a reference data set comprising stored digital image data on an eye of a patient, the stored image data having been collected with the patient in a pre-surgical position and including image data on an extracorneal eye feature;
    collecting a real-time data set comprising real-time digital image data on the patient eye in a surgical position different from the pre-surgical position, the real-time image data including image data on the extracorneal eye feature;
    removing, by the one or more processors, pixel data from a first set of pixels of the reference data set to yield a reduced reference data set;
    removing, by the one or more processors, pixel data from a second set of pixels of the real-time data set to yield a reduced real-time data set, the first set disjoint from the second set;
    displaying a combined image comprising a superposition of the reduced reference and the reduced real-time data sets;
    determining whether the combined image indicates an adequate registration between the reference and the real-time data sets based upon the extracorneal eye feature data in the reduced reference and the reduced real-time data sets; and
    if the registration is not adequate, manipulating one of the reduced reference and the reduced real-time data sets until an adequate registration is achieved.

2. The method recited in claim 1, wherein the pre-surgical position is upright and the surgical position is prone.

3. The method recited in claim 1, wherein the stored image data comprise camera data organized in pixels.

4. The method recited in claim 1, wherein the collecting step is performed using a video camera.

5. The method recited in claim 1, wherein the collecting step is performed continuously during the surgery.

6. The method recited in claim 1, wherein the extracorneal eye feature comprises a blood vessel in a sclera of the eye.

7. The method recited in claim 1, further comprising the step, prior to the displaying step, of scaling one of the reduced reference and the reduced real-time data sets to the other of the reduced reference and the reduced real-time data sets in order to equalize a display size of the reduced reference and the reduced real-time data sets displayed in the superimposed image.

8. The method recited in claim 1, further comprising the step of determining a preferred center of a cornea of the eye in the reference data set.

9. The method recited in claim 8, further comprising the step, following the preferred center determining step, of displaying an image of the reference data set with an indicium superimposed thereon comprising a reticle centered on the determined preferred cornea center.

10. The method recited in claim 9, wherein the reticle comprises a pair of substantially perpendicular lines intersecting at the determined preferred cornea center.

11. The method recited in claim 10, wherein the reticle further comprises a plurality of substantially perpendicular hatch marks disposed substantially equidistantly along the lines.

12. The method recited in claim 10, wherein the reticle further comprises a circle substantially smaller than the cornea having a center at the determined preferred cornea center.

13. The method recited in claim 8, further comprising the step of determining a location of a limbus of the eye in the reference data set.

14. The method recited in claim 13, further comprising the step of displaying the reference data set with a second indicium superimposed thereon comprising a circle centered on the determined preferred cornea center and positioned along the determined limbus location.

15. The method recited in claim 1, further comprising the steps of:
    displaying the reference data set;
    locating the extracorneal eye feature in the displayed reference data set; and
    wherein the registration determining step comprises determining whether the images of the extracorneal eye feature from the reference data set and from the real-time data set are aligned in the combined image, an adequate alignment corresponding to an adequate registration.

16. The method recited in claim 1, wherein the combined image displaying step comprises:
    summing the reduced reference data set and the reduced real-time data set to obtain a superimposed image wherein each pixel contains data from only one of the reduced reference data set and the reduced real-time data set to form the combined image.

17. The method recited in claim 16, claim 1, wherein removing, by the one or more processors, pixel data from the first set of pixels of the reference data set comprises removing pixel data from alternate pixels.

18. The method recited in claim 1, wherein removing, by the one or more processors, pixel data from the first set of pixels of the reference data set comprises determining a location of a limbus of the eye in the reference data set and removing data from all pixels circumscribed by the limbus.

19. The method recited in claim 1, wherein removing, by the one or more processors, pixel data from the first set of pixels of the reference data set comprises removing pixel data from alternate pixels outside the limbus.

20. The method recited in claim 1, further comprising the step of, if the registration is adequate, performing the eye surgery.

21. The method recited in claim 20, further comprising performing the collecting, displaying, determining, and manipulating steps at predetermined intervals throughout the surgery.

22. The method recited in claim 20, wherein performing the eye surgery comprises forming a desired corneal profile to be achieved with an excimer laser.

* * * * *